United States Patent
Michel et al.

(10) Patent No.: US 8,913,714 B2
(45) Date of Patent: Dec. 16, 2014

(54) DETECTOR ARRANGEMENT AND X-RAY TOMOGRAPHY DEVICE FOR PERFORMING PHASE-CONTRAST MEASUREMENTS AND METHOD FOR PERFORMING A PHASE-CONTRAST MEASUREMENT

(75) Inventors: Thilo Michel, Nürnberg (DE); Peter Bartl, Puschendorf (DE); Gisela Anton, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 397 days.

(21) Appl. No.: 13/264,554
(22) PCT Filed: Apr. 13, 2010
(86) PCT No.: PCT/EP2010/054789
§ 371 (c)(1),
(2), (4) Date: Oct. 14, 2011
(87) PCT Pub. No.: WO2010/119019
PCT Pub. Date: Oct. 21, 2010

(65) Prior Publication Data
US 2012/0033785 A1    Feb. 9, 2012

(30) Foreign Application Priority Data
Apr. 17, 2009  (DE) .......................... 10 2009 019 306

(51) Int. Cl.
| | | |
|---|---|---|
| H05G 1/64 | (2006.01) |
| H05G 1/08 | (2006.01) |
| H01L 27/148 | (2006.01) |
| H01L 27/146 | (2006.01) |
| G01T 1/29 | (2006.01) |
| G01N 23/20 | (2006.01) |
| A61B 6/00 | (2006.01) |

(52) U.S. Cl.
CPC .......... G01N 23/20075 (2013.01); A61B 6/484 (2013.01)
USPC ........................ 378/22; 378/98.8; 250/370.09

(58) Field of Classification Search
CPC ......... G01T 1/241; G01T 1/242; G01T 1/243; G01T 1/20; G01T 1/24; G01J 1/4228; A61B 6/484; G02B 27/44
USPC ................ 378/37, 98.12, 21–27, 62, 98, 210; 382/130; 250/370.01, 370.08, 370.09, 250/370.14
See application file for complete search history.

(56) References Cited

U.S. PATENT DOCUMENTS
5,812,629 A * 9/1998 Clauser .......................... 378/62
6,226,353 B1   5/2001 Wilkins et al.
(Continued)

FOREIGN PATENT DOCUMENTS
CN  1247687 A    3/2000
CN  101257851 A  9/2008
(Continued)

OTHER PUBLICATIONS

Weitkamp et al.; "Hard x-ray phase imaging and tomography with a grating interferometer", Proceedings of the SPIE, vol. 5535, pp. 137-142 (2004), Publication Date: Oct. 2004; Others; 2004.

(Continued)

Primary Examiner — Anastasia Midkiff
(74) Attorney, Agent, or Firm — Harness, Dickey & Pierce (57) ABSTRACT

A detector arrangement is disclosed for performing phase-contrast measurements, including at least two transducer layers arranged one behind the other, wherein at least the first transducer layer arranged in the radiation direction includes alternate sensitive areas having a high absorptance for the conversion of incident radiation quanta into signals and less sensitive areas having a lower absorptance in comparison thereto. Further, a corresponding X-ray tomography device and a method for performing phase-contrast measurements are also enclosed.

22 Claims, 9 Drawing Sheets

(56) References Cited

U.S. PATENT DOCUMENTS

| | | |
|---|---|---|
| 2002/0041653 A1 | 4/2002 | Wilkins et al. |
| 2009/0092227 A1 | 4/2009 | David et al. |
| 2009/0128830 A1* | 5/2009 | Kottler et al. ............ 356/521 |

FOREIGN PATENT DOCUMENTS

| | | |
|---|---|---|
| EP | 1731099 A1 | 12/2006 |
| JP | 2003116826 A | 4/2003 |
| JP | 2008197593 A | 8/2008 |

OTHER PUBLICATIONS

A. Olivo et al.; "A multilayer edge-on single photon counting silicon microstrip detector for innovative imaging techniques in diagnostic radiology"; Review of Scientific Instruments, AIP Melville, NY, US LNKD-DOI:10.1063/1.1582390, vol. 74, No. 7, Jul. 2003, pp. 3460-3465, XP0120409421SSN:0034-6748; Others.

International Search Report for International Application No. PCT/EP2010/054789 dated Apr. 13, 2010.

* cited by examiner

DETECTOR ARRANGEMENT AND X-RAY TOMOGRAPHY DEVICE FOR PERFORMING PHASE-CONTRAST MEASUREMENTS AND METHOD FOR PERFORMING A PHASE-CONTRAST MEASUREMENT

PRIORITY STATEMENT

This application is the national phase under 35 U.S.C. §371 of PCT International Application No. PCT/EP2010/054789 which has an International filing date of Apr. 13, 2010, which designated the United States of America, and which claims priority on German patent application number DE 10 2009 019 306.5 filed Apr. 17, 2009, the entire contents of each of which are hereby incorporated herein by reference.

FIELD

At least one embodiment of the invention generally relates to a detector arrangement and X-ray tomography device for performing phase-contrast measurements and also at least one embodiment of the invention generally relates to a method for performing a phase-contrast measurement.

BACKGROUND

Two effects can primarily be observed during imaging by ionizing rays, especially by X-rays, which occur as the radiation passes through the material, namely absorption and phase shifting of the radiation passing through an object. It is also known that in many cases, when a ray passes through an object under examination, the phase shift depends significantly more greatly on small differences with regard to the thickness and the composition of the penetrated material than the absorption. Basically the extent of the two effects depends in each case on the energy of the radiation, the density and the atomic number of the irradiated material.

The passage of X-rays through material can be described by a complex refractive index. The non-disappearing imaginary part of the refractive index describes the strength of the absorption of the material. The non-disappearing real part of the refractive index leads to a phase shift of the X-ray wave passing through the material. The object of phase-contrast X-ray imaging is, in addition to images of the absorption strength expressed by the linear coefficient of attenuation or the imaginary part of the refractive index of the object irradiated by the X-rays, to also measure images of the local phase or of the local gradients of the phase of the wave front running through the irradiated object.

In this case, in a similar way to X-ray radiography or X-ray tomography, both projectional images of the phase shift and also tomographic representations of the phase shift can be computed on the basis of a plurality of projectional images.

The phase of an X-ray wave cannot be directly determined in such cases but only by interference with a reference wave. The phase shifts relative to the reference waves or to the adjacent rays respectively can be measured by using interferometric gratings and be combined into projectional and/or tomographic recordings.

A structure of an X-ray tomography device which is suitable for carrying out phase-contrast measurements is known from EP 1 731 099 A1. In this structure a total of three gratings are needed. A first grating G0, which is also referred to as the source grating, is placed between the focal point of the X-ray tube and the position of the object. The second grating G1, which is referred to as the diffraction grating, phase grating or also Talbot grating, is placed between the object and the X-ray detector. The third grating G2 is referred to as the absorption grating and is arranged between the diffraction grating G1 and the X-ray detector.

The source grating G0 serves to provide a plurality of line sources which behave spatially partly coherent in relation to each other. The diffraction grating G1 serves to impress a spatial phase shift pattern on the incident wave front and thus to create an interference pattern behind the diffraction grating G1. At specific distances from this grating G1, at the Talbot distances, on arrival of a smooth wave at the grating G1, a more or less sharp interference pattern is produced. The absorption grating G2 serves to sample the interference pattern. The gratings G0, G1 and G2 are aligned in parallel to each other in such cases.

The detector is structured for locally-resolved detection of the electrical signals generated by conversion of incident radiation quantas in the form of pixels. The recording of an absorption image and of a phase-contrast image or of a differential phase-contrast image is undertaken in the known manner by measuring the intensity in each pixel of the detector as a function of the relative position of the gratings G0, G1 and G2 in relation to each other. In the known case for example the absorption grating G2 is shifted step-by-step or continuously perpendicular to the radiation direction and perpendicular to the slot direction. The intensity of the X-ray radiation is registered for each pixel in the form of an electrical signal as a function of the grating position. A modulated signal is involved here, which in the respective pixel represents the strength of the absorption in the ray path through the object to the pixel from the illuminated part of the grating G2. From the position of the maxima and minima of the intensity curve in the pixel, which depends on the projected gradient of the real part of the refractive index, the local phase shift of the X-rays can be computed. An integration of these gradients along a line perpendicular to the radiation direction and perpendicular to the slot direction delivers the local average phase of the wave front after its passage through the object projected onto the pixel.

The disadvantage of the known method is that in the absorption grating G2 radiation quantas which have passed the object will be absorbed and will thus no be longer available for imaging. This especially increases the dose necessary for imaging or the patient dose. A further disadvantage can be seen in the fact that changes in the geometry of the arrangement during the measurement of the intensity, for example with a change to a relative position of the gratings in relation to one another lead, through mechanical deformations as a result of centrifugal forces, as arise in CT applications, to a distorted modulation curve. This leads to an incorrect determination of the phase.

SUMMARY

At least one embodiment of the invention is directed to a detector arrangement, an X-ray tomography device and/or a method for phase-contrast measurement so that a dose stress for an object under examination is reduced while the image quality remains the same.

Advantageous embodiments and developments are the subject matter of subclaims.

The detector arrangement of least one embodiment for carrying out phase-contrast measurements comprises at least two transducer layers arranged behind one another, wherein at least the first transducer layer arranged in the radiation direction comprises alternate sensitive areas in each case having a high absorptance for the conversion of incident X-ray quantas into signals and less sensitive areas having a lower absorptance by comparison thereto.

Radiation direction in this context is to be understood as the direction from which, when the detector arrangement is being used in accordance with specifications, X-ray radiation strikes the detector arrangement. Each transducer layer is part of a detector of the detector arrangement. The detector includes all modules which are needed for converting the X-ray radiation into electrical signals and for reading out the electrical signals. Depending on which unit is considered below, transducer layers can be taken to mean transducer layers arranged behind one another or detectors arranged behind one another. The term "sensitive area" is to be understood as the area of a transducer layer in which the radiation quantas interact with the transducer layer with the object of generating an electrical signal. The term "less sensitive area" does not mean the measure necessary for pixelating the transducer layer, especially the area of septa. Instead this is to be understood as specifically embodied areas in which the radiation quantas for a conversion in the direction of a second transducer layer arranged downstream from the first transducer layer can pass.

With such a detector arrangement the previously used absorption grating G2 can be dispensed with in a phase-contrast measurement. It has been recognized that for the sampling of the generated interference pattern it is sufficient to let a part of the radiation quantas in a spatial pattern interact in the first transducer layer, while the remaining part of the radiation quantas which strikes the intermediate areas of the pattern, can pass the first transducer layer and is available in the second transducer layer arranged behind it in the radiation direction for a signal generation. The spatial pattern in the first transducer layer is formed in each case by alternate sensitive areas with a high absorptance for the conversion of incoming radiation quantas into signals and less sensitive areas with a lower absorptance by comparison thereto. The transducer layers are located in a fixed spatial position and orientation relative to one another.

Thus almost all radiation quantas passing through the object are used for imaging. In this case, no radiation quantas are lost without being used in an absorption grating G2. This reduces the X-ray dose which is necessary to generate a phase-contrast image with corresponding similar quality.

The two transducer layers arranged behind one another and the pattern impressed into the first transducer layer mean that the interference pattern is sampled for each measurement at two different positions. Compared to the known configuration, this means that only half as many measurements are needed. The proposed measure thus also shortens the recording time needed. This also reduces the movement artifacts present in the reconstructed image.

An X-ray tomography device with such a detector arrangement, because the absorption grating G2 has been dispensed with, is also less complex in its structure and is less susceptible to mechanical stresses, such as typically occur during rotation of a recording system in a computed tomography device. The signal curves recorded, and thus the local phase differences derived therefrom, are thus able to be determined with a greater degree of security.

Structuring into sensitive and less sensitive areas is especially merely required for the first transducer layer, so that the available transducer layers can be used without further modification.

In an advantageous embodiment of the invention, the second transducer layer also has such sensitive areas and less sensitive areas, with there being one of the less sensitive areas of the second transducer layer in the direction of radiation behind one of the sensitive areas of the first transducer layer in each case and correspondingly there being one of the sensitive areas of the second transducer layer behind one of the less sensitive areas of the first transducer layer. Detectors D1 and D2 can be of an identical construction, but can be displaced in relation to one another.

In an advantageous embodiment of the invention, the absorptance of the less sensitive areas is reduced at least by a factor of 0.5 by comparison with the absorptance of the sensitive areas. The decisive factor here is that the less sensitive areas, by comparison with the sensitive areas, have a markedly lower absorptance probability, 50 W for example. It would be especially advantageous in the interests of maximum dose savings for the less sensitive areas to be quasi-transparent for the X-ray radiation used.

Sensible widths of the sensitive areas and/or the less sensitive areas lie in a range of between 100 nm and 100 µm. The sensitive areas and/or the less sensitive areas preferably have a width of 0.5 µm to 20 µm. The areas are dimensioned in this case so that a generated interference pattern locally resolved can be sampled sufficiently precisely.

The sensitive areas and the less sensitive areas are advantageously each embodied in the form of strips. The strips of the two transducer layers can advantageously run parallel to one another and for integration into an X-ray tomography device are aligned in parallel to the strips of the first and second grating G0 and G1. The two transducer layers are also preferably structured for locally-resolved conversion of the incident radiation quantas into pixels corresponding to one another.

In a further advantageous embodiment, each pixel covers a number, preferably hundreds, of sensitive areas and a number, preferably hundreds, of less sensitive areas. Depending on pixel size the number of the sensitive and less sensitive areas can amount to between ten and four hundred. It has been recognized that a number of sensitive and less sensitive areas can be located in each pixel, without this resulting in a noticeable disruption by scattering of the X-ray radiation between the areas, and without the passing of the released photo or Compton electrons through a number of areas resulting in appreciable problems.

The inventors have also recognized that, on the basis of an evaluation of signals detected rapidly after one another over time with a fixed sampling geometry, movement artifacts in the reconstructed image can be detected and reduced. To do this, during the intensity recording at each fixed relative position of the gratings and of the transducer layers, the intensity signal must be sampled in a rapid temporal sequence.

In an advantageous embodiment of the invention, readout electronics which are in electrical contact with the respective transducer layer are thus arranged behind the transducer layers. The associated short signal lines enable signals to be detected in a rapid temporal sequence. It would however be just as conceivable for the signals to be taken out via signal lines contained therein from the irradiated area of the detector arrangement and only subsequently conveyed to read-out electronics. The components of the read-out electronics do not influence the signal generation in a disruptive manner in this case. The components additionally do not have to be resistant to X-ray radiation, enabling commercially available components to be used.

The temporal intensity curve can then be compared in pixels of the two transducer layers practically lying behind one another and temporal correlations can be searched for. A decreasing intensity in the pixel in the first transducer layer with simultaneous increasing intensity in the pixel of the second transducer layer lying behind it points to a change in the geometry, e.g. as a result of a movement of the focus or of the grating G0, a movement in the object or a change to the geometry as a result of mechanical deformations. This geometry change can then be corrected and the quality of the reconstructed images (absorption and phase images) can be improved. In computed tomographic geometry in particular this can be important because of the high centrifugal forces to be expected there. Since these temporal correlations of the signals in the pixels of the two transducer layers are to be determined during each relative position of the gratings, focuses, detectors in relation to one another during each scan step, the time between movement to two relative positions can be used to read out the detectors.

For this purpose it can be advantageous for the read-out electronics to have signal memories assigned to each pixel that are designed for buffering a sequence of the electrical signals recorded rapidly after one another in time.

The intensity signals in this case can be stored in analog form or digitally time-resolved in a rapid temporal sequence of for example one microsecond locally in electronics close to the electrode of the semiconductor detector or the photodiode of the scintillation detector and can be read out during the move to the next position for sampling the interference pattern. For example the detectors, if they are counting semiconductor detectors, can contain not only one counter in each pixel but a number, for example 16 counters. These counters are used one after another for counting events in narrow time windows. The counter depth of each individual counter can thus be selected lower than the counter depth for use of a single counter. The counters are filled one after another. When moving to the new relative position between gratings, focus and detector arrangement or during the adjustment of a subsequent sampling geometry, all counters of all pixels are read out.

For detectors operating in an integrating manner there is the option of the use of a chain of capacitors, which are filled one after the other with the charge to be measured. The reading out and possible amplification and digitization of the intensity signal is undertaken during the movement to the new relative position between gratings, focus and detectors.

A second aspect of at least one embodiment of the invention relates to an X-ray tomography device for performing phase-contrast measurements which comprises an X-ray source with a coherence means for generating quasi-coherent X-rays, a diffraction grating arranged in the direction of the radiation behind an area under examination for generating an interference pattern and a previously described detector arrangement, with the detector arrangement and/or the diffraction grating and/or the coherence means being assigned an adjustment means with which the relative locations of at least two of these components is able to be continuously or discretely changed perpendicular to the radiation direction.

In an advantageous example embodiment the coherence means is a source grating. The source grating serves to provide a plurality of line sources which behave spatially in a partly coherent manner in relation to one another.

Another option for providing a number of individual spatially coherent sources consists of realizing a number of focuses, which as such provide a sufficiently large spatial coherence length, through suitable electronic optics in the X-ray tube. The coherence means in this case thus comprises electronic optics for generating a plurality of focuses.

As an alternative the coherent X-ray radiation can also be generated by way of a focus with a small extent and correspondingly high X-ray power, for example by using microfocus or nanofocus X-ray tubes.

To set different sampling geometries the source grating G0 can be displaced with the adjustment means perpendicular to the radiation direction, whereby in both detectors of the detector arrangement in each pixel the intensities are then able to be recorded as a function of the relative position of the gratings G0, G1 and of the detectors. The two detectors, i.e. the detector arrangement as such, can also be moved jointly with one another laterally, i.e. perpendicular to the strips, in order to sample the interference pattern. The focuses in the X-ray tube can also be adjusted by way of the electron optics by deflecting the electron beam.

A second aspect of at least one embodiment of the invention relates to a method for performing phase-contrast measurements with a previously described X-ray tomography device, in which at each sampling position for different relative locations perpendicular to the radiation direction between at least two of the components coherence means, diffraction grating and detector arrangement, electrical signals for the pixels of the two transducer layers are read out and computed into a phase-contrast image.

Preferably, for the different relative locations of the at least two components, a sequence of electrical signals is recorded for the pixels of the two transducer layers and computed for a movement correction of the phase-contrast image and/or used for detection and for correction of a changed sampling geometry.

BRIEF DESCRIPTION OF THE DRAWINGS

The invention will be explained in greater detail below with reference to example embodiments and with reference to drawings, in which.

In the figures elements which are the same or which have the same function are labeled with the same reference characters. For repeating elements in a figure only one element is provided with a reference character in each case for reasons of clarity. The diagrams in the figures are schematic and not necessarily true-to-scale, with scales able to vary between the figures.

DETAILED DESCRIPTION OF THE EXAMPLE EMBODIMENTS

Figure 1:
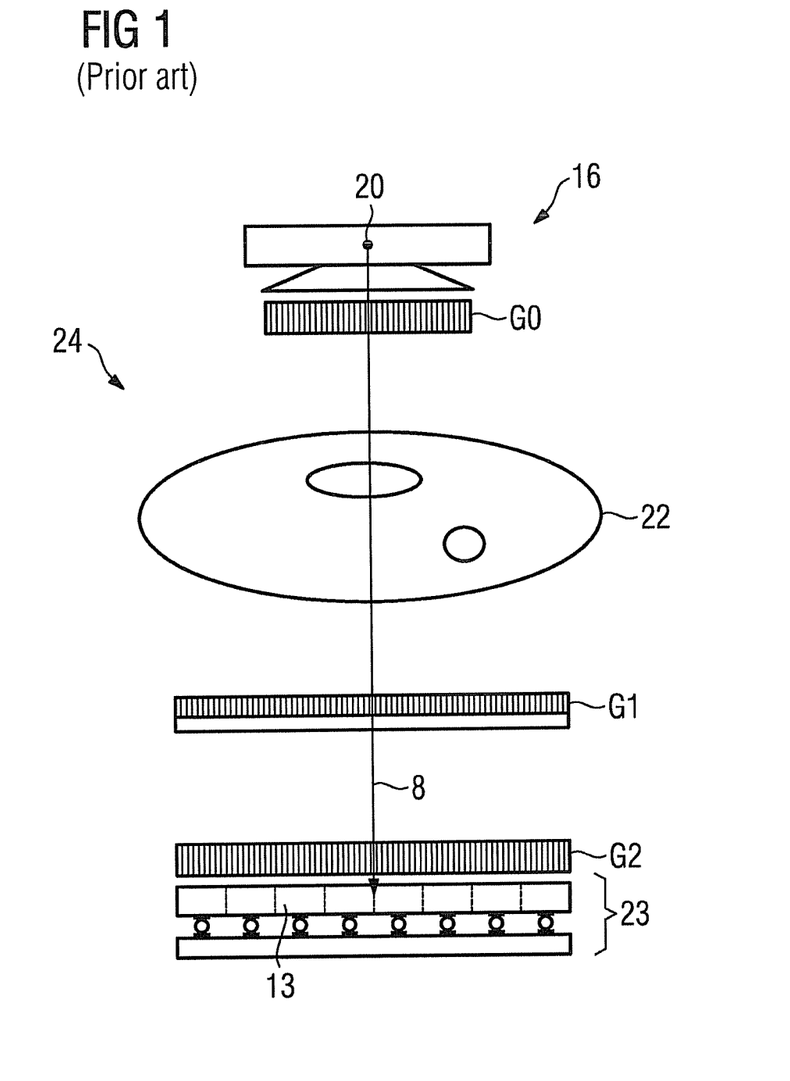
FIG. 1 shows a side view of a layout of a grating interferometer in accordance with the prior art.

FIG. 1 shows a basic layout, viewed from the side, of a grating interferometer 24 according to the prior art. A total of three gratings G0, G1, G2, are needed for phase-contrast measurement. Outgoing X-ray radiation from a focus 20 of an X-ray source 16, for example an X-ray tube, passes through the first source grating G0 close to the source. The source grating G0 serves to provide a plurality of line sources which behave in a partly coherent manner spatially in relation to one another. This grating G0 is manufactured for example on the basis of a silicon substrate or a polymer substrate, in which slots are inserted by lithographic methods, by LIGA methods or by etching methods for embodying the grating G0. The distance between adjacent slot centers, the width of a slot as well as the thickness of the substrate used lie in a range of the order of magnitude of micrometers. The slot depth is selected as large as possible and amounts in this example to a few hundred micrometers. The slots are filled with a material different from the substrate with preferably high absorption capabilities for the X-ray radiation to be used. The filler material is gold for example. The quasi-coherent X-ray radiation generated in this way penetrates an object, with a phase shift depending on the structure of the object occurring during its passage through the object 22.

The X-ray radiation modified in this way subsequently passes through a diffraction grating G1. The diffraction grating G1 serves to impress a spatial phase-shift pattern on the incident wave front and thus to generate an interference pattern behind the diffraction grating G1. At specific distances from this grating G1, the so-called Talbot distances, a constructive interference pattern is produced on arrival of a smooth wave at integer distances on the grating G1. The diffraction grating G1 is based for example on a silicon substrate or polymer substrate, from which steps have been formed by photolithographic methods or etching methods. The distance, the width, the height of the steps in the substrate as well as the thickness of the substrate used lie in the order of magnitude of micrometers.

The interference pattern embodied in this way is sampled with the aid of an absorption grating G2 at the downstream detector 23 and its pixels 13 or detector elements. Like the source grating G0, it is manufactured on the basis of a silicon substrate or polymer substrate, with slots being formed by photolithography methods or etching methods. The distance between the slot centers and the width of the slots lies in the order of magnitude of a few micrometers or less. The thickness of the substrate used and the slot depth amounts in the present example to a few hundred micrometers. The slots are filled with a material different from substrate, preferably with a high absorption capability for the X-ray radiation to be used.

The slots of the source grating G0 are arranged parallel to the slots of the absorption grating G2 and parallel to the steps of the diffraction grating G1. The gratings G0, G1, G2 are irradiated in the direction of their thicknesses.

Phase-contrast measurement is undertaken in the known manner by measuring the intensity in the each pixel 13 of the detector 23 as a function of the relative position of the gratings G0, G1 und G2 to one another. In the known case the absorption grating G2 is for example shifted in steps perpendicular to the radiation direction 8 and perpendicular to the slot direction. The intensity of the X-ray radiation is registered for each pixel 13 in the form of an electrical signal as a function of the grating position. The signal involved is a modulated signal which in the respective pixel 13 represents the strength of the absorption in the radiation path through the object 22 to the pixel from the illuminated part of the absorption grating G2.

If for example a specific pixel 13 of the detector 23 is considered and the measured intensity is entered as a function of the relative position of the absorption grating G2, then a periodic, sine wave-like curve of the intensity is obtained at this pixel 13. If these measured radiation intensities are analyzed for each pixel 13 as a function of the grating offset, then the phase shift and the relative phase shift between the pixels can be determined for each pixel 13. The positions of the maxima and minima of the intensity curve in pixel 13 namely relate to the projected gradient of the real part of the refractive index. An integration of these gradients along a line perpendicular to the radiation direction 8 and perpendicular to the slot direction delivers the local average phase shift of the wave front after its passage through the object 22 projected onto the pixel 13.

As already discussed, the disadvantage which arises with the known grating interferometer is that X-rays are absorbed unused for imaging by the absorption grating G2. With the layout of the imaging system of an X-ray tomography device 15 depicted in FIG. 2 seen from the side this disadvantage is largely avoided. The X-ray tomography device 15 can for example be CT device, a C-arm device, mammography device or an X-ray device for examination of objects or material, for example a baggage scanner.

Figure 2:
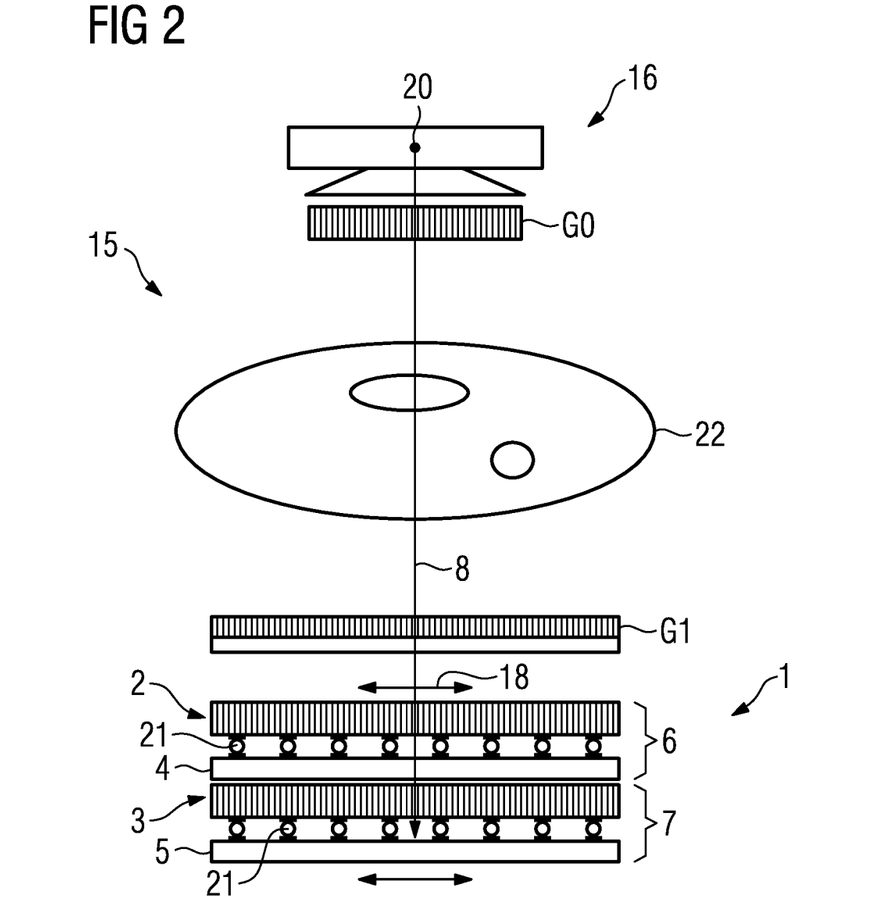
FIG. 2 shows a side view of a first X-ray tomography device with an embodiment of an inventive detector arrangement.

The X-ray tomography device 15 is characterized by a detector arrangement 1, in which two transducer layers 2, 3 are arranged behind one another in the radiation direction 8 and are structured or designed so that for each measurement, measurement data for the interference pattern is detected which corresponds to the measurement data at two adjacent adjustment positions when using a conventional absorption grating G2. For each measurement twice as many measurement values are thus recorded as with the grating-based measurement of the interference pattern. This doubles the sampling speed required overall, which leads to smaller movement artifacts in the image. Read electronics 4, 5 are arranged behind each transducer layer 2, 3 in each case, which make electrical contact via electrical contacts 21 with the transducer layer 2, 3. The associated short signal routes make it possible to record the signals in a rapid time sequence. The unit comprising transducer layer and read-out electronics 2, 4 and 3, 5 in itself represents a detector 6, 7 in each case. The detector arrangement 1 thus involves two detectors 6, 7 arranged behind one another. Adjustment means 18 are assigned to the detector arrangement 1, with which the entire detector arrangement 1 for consecutive measurements is able to be adjusted to the next sampling position perpendicular to the radiation direction 8.

The detectors 6, 7 in the present example embodiment involve counting semiconductor detectors with which the absorption events are able to be detected as a count and/or energy-resolved. In this case the two transducer layers 2, 3 are directly converting and comprise a doped semiconductor material based on selenium, silicon, CdTe, CZT, GaAs or HgI. However an indirectly-converting detector 6, 7 can also be used. In this case the signals are generated in two stages via the generation of light impulses with a transducer layer 2, 3 in the form of a scintillator. Possible options for the scintillating material can be a plastic scintillator, NaI, CsI, Gadolinium oxysulfide or LSO.

Figure 3:
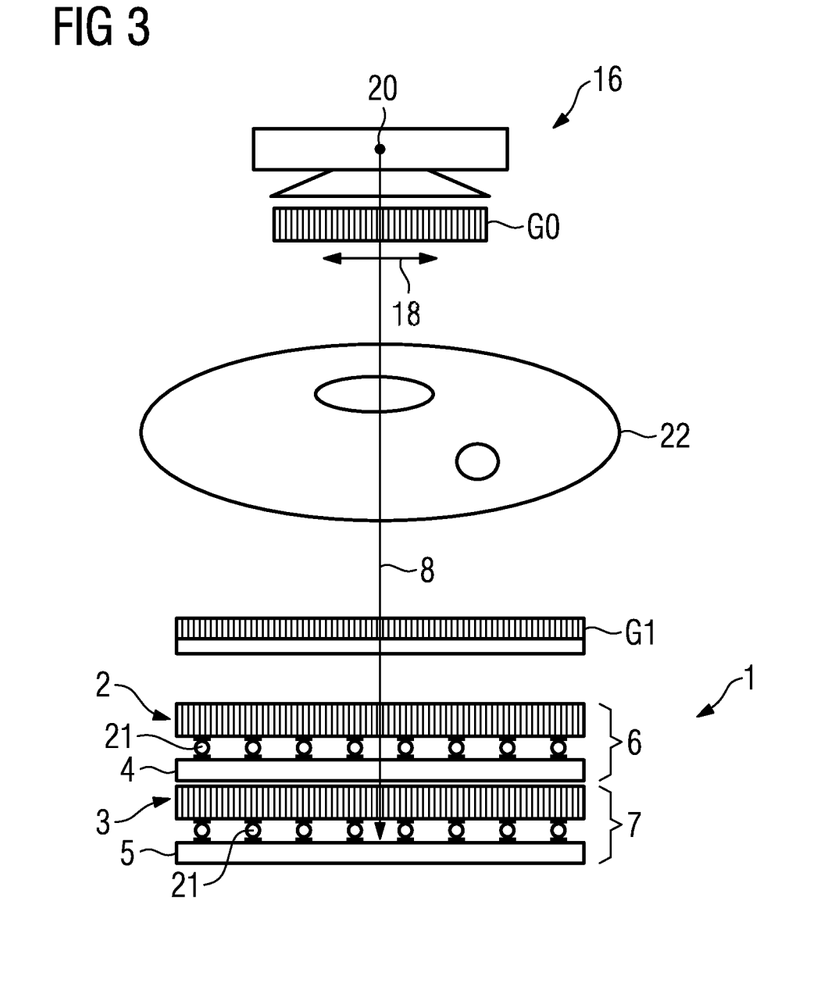
FIG. 3 shows a side view of a second X-ray tomography device with the detector arrangement.

As is shown in FIG. 3 the interference pattern can also be sampled with a stationary detector arrangement 1 and an adjustment of the source grating G0. In this case the source grating G0 is assigned a corresponding adjustment means 18.

Figure 4:
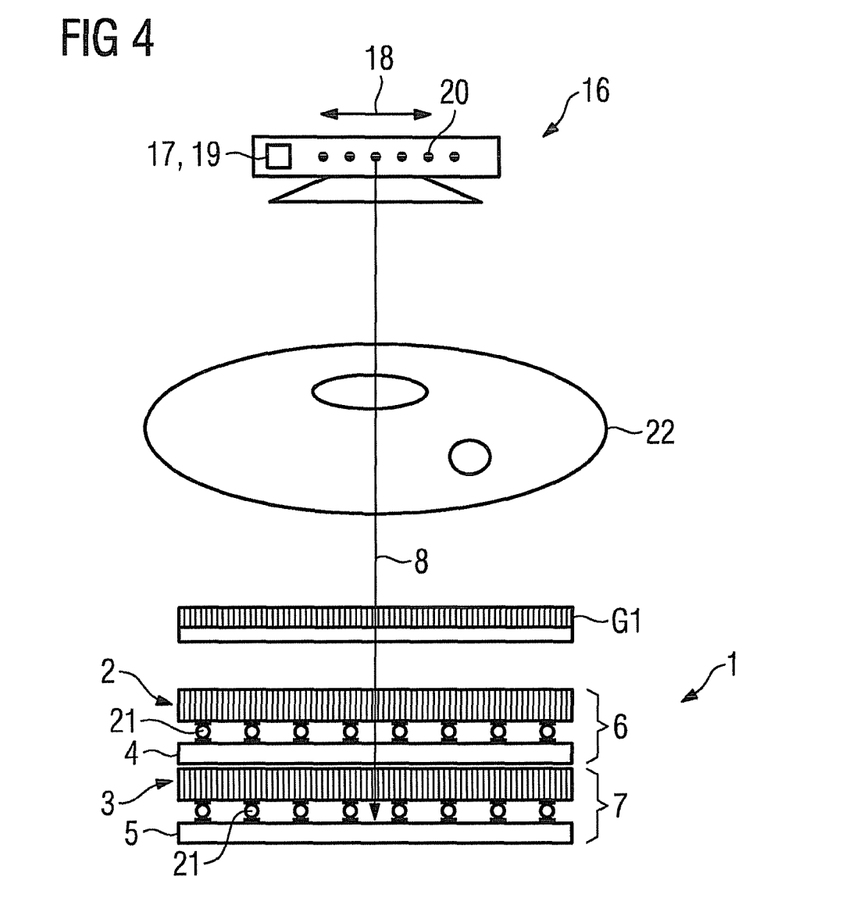
FIG. 4 shows a side view of a third X-ray tomography device with the detector arrangement.

In FIG. 4 electron optics 19 for generating a plurality of focuses 20 are used as coherence means 17 instead of the source grating G0, with the focuses 20 being adjusted for sampling the interference pattern by means of the adjustment means assigned to the electron optics 19.

Figure 5:
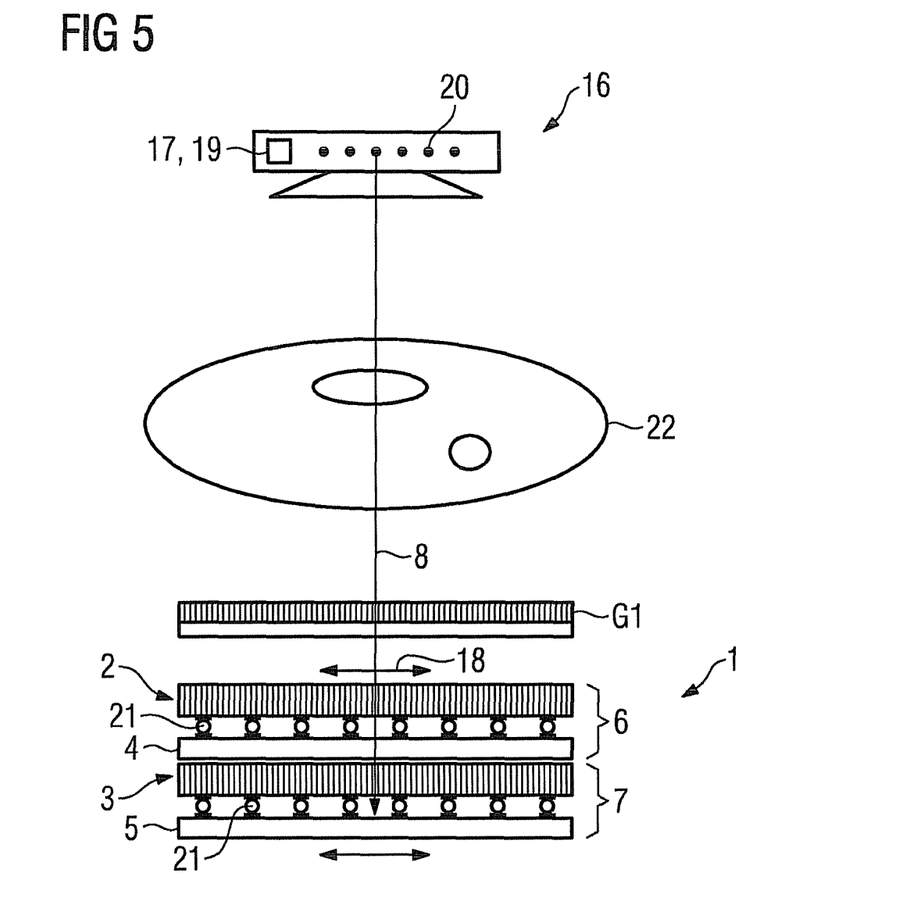
FIG. 5 shows a side view of a fourth X-ray tomography device with the detector arrangement.

Likewise, in accordance with the example embodiment depicted in FIG. 5, for stationary generation of a one-dimensional focuses array 20 the detector arrangement 1 can naturally be adjusted accordingly via an adjustment means 18. The only decisive factor is that between two sampling positions the relative locations between two of the components source grating G0, diffraction grating G1 and detector arrangement 1 are able to be adjusted perpendicular to the radiation direction 8.

Figure 6:
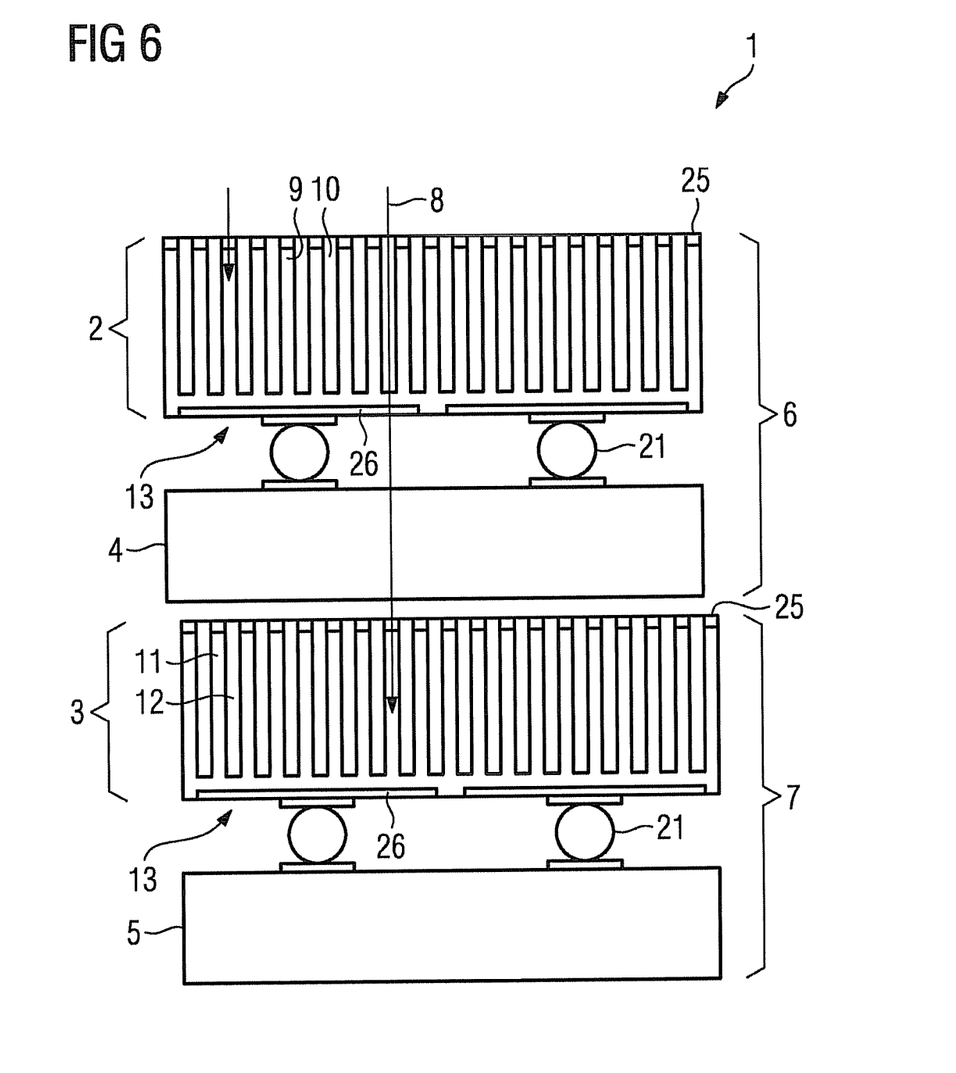
FIG. 6 shows a section from a first detector arrangement, viewed from the side.

FIG. 6 shows a side view in the direction of the strips of a section of an inventive detector arrangement 1 in accordance with a first example embodiment. The detectors 6, 7 are counting semiconductor detectors. The less sensitive areas 10, 12 are introduced into the semiconductor material by slots or channels created by photolithographic methods, etching methods or lasers. In these areas formed in this way the X-rays are not or are to all intents and purposes not attenuated and can pass through the detector 6, 7. Manufacturing is thus undertaken using a fully sensitive semiconductor layer as its starting point. The sensitive areas 9, 11 and less sensitive areas 10, 12 form strips which run perpendicular to the plane of the drawing. The strips 9, 10, 11, 12 are the same size. The width of each strip 9, 10, 11, 12 amounts in this example to 10 μm and usually lies within a range of 0.5-20 μm. The strips 9, 10, 11, 12 can however also be of different sizes and have a strip width in a range of 0.5 μm to 20 μm.

The detectors 6, 7 are structured into individual pixels 13. For this purpose an opposing electrode 25 is arranged on the first side of the transducer layer 2, 3 in the radiation direction 8 and a pixel electrode 26 is arranged on the second side of the transducer layer 2, 3, between which for separation of the electrons and holes released by interaction processes with incident X-ray quantas, a voltage is applied. The pixel pitch amounts to approximately 10 or more micrometers, so that a number of sensitive and less sensitive strips 9, 10, 11, 12 are covered by a pixel 13. In addition it would be possible to construct a semiconductor detector by rods of the transducer layer 2, 3 having an n-doped area at their tip and a p-doped area on the opposite side of the transducer layer 2, 3 for embodying the pixel 13.

With indirectly-converting detectors 6, 7 the transducer layers 2, 3 by contrast are a scintillator in which the less sensitive areas 10, 12 are formed by slots, photolithographic methods, etching methods or by slots or channels created by lasers. The less sensitive areas 10, 12 can thus be implemented on a fully-sensitive transducer layer or an initially unstructured scintillator. The intensity measurement is realized in pixels 13 of for example a few 10 μm pixel pitch by coupled-on photodiodes.

The released charge carriers are collected in a coupled-on TFT array or in read-out electronics and/or processing electronics coupled on by electrical contacts 21 in the form of bump bonds or wire bonds in the form of an ASIC. The semiconductor detectors can be operated in an integrating or counting mode.

The areas 9, 10, 11, 12 of the two transducer layers 2, 3 are arranged offset in relation to one another so that a sensitive strip 11 of the second transducer layer 3 is arranged in each case below a less sensitive strip 10 of the first transducer layer 2. The detector arrangement 1 can be formed from two identically constructed detectors 6, 7 which are arranged with an offset in relation to one another.

Figure 7:
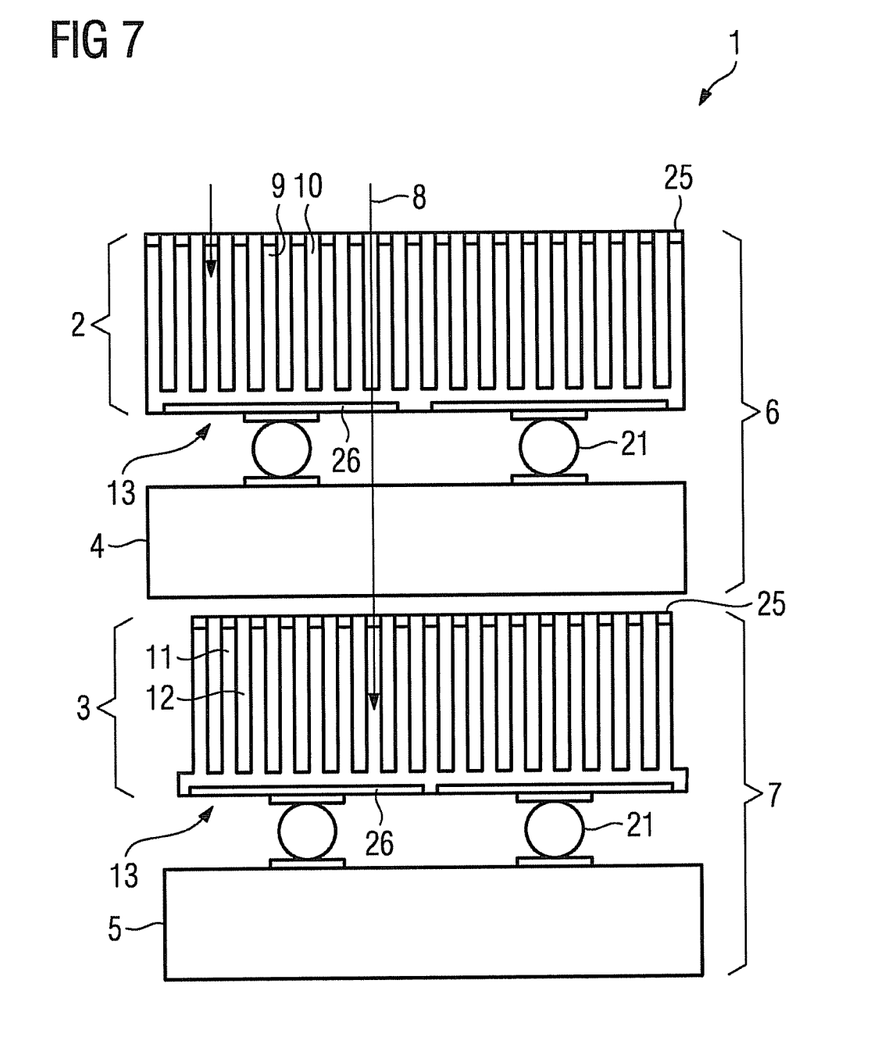
FIG. 7 shows a section from a second detector arrangement, viewed from the side.

FIG. 7 shows a detector arrangement 1 in which the two detectors 6, 7 are not identically constructed. The position of the pattern of slots or of the sensitive and less sensitive areas 9, 10, 11, 12 in relation to the pixel electrode 26 in the first transducer layer 2 is shifted in relation to the position of the pattern of the slots or of the sensitive and less sensitive areas 9, 10, 11, 12 in relation to the pixel electrode 26 in the second transducer layer 3.

Figure 8:
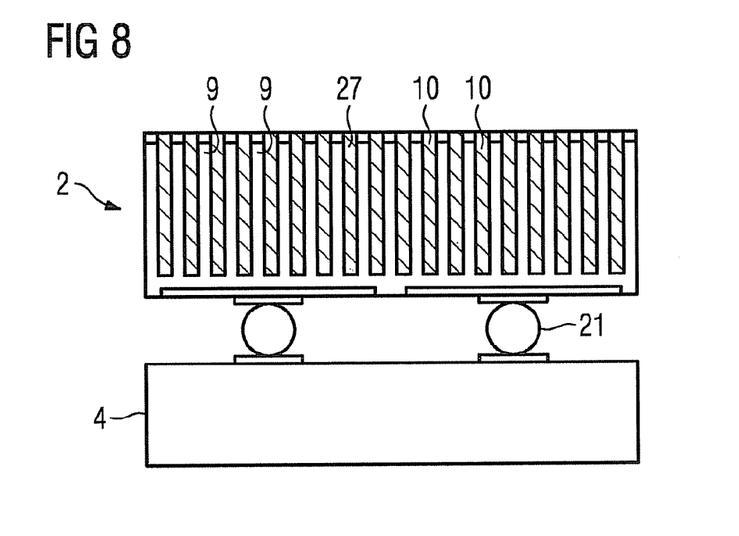
FIG. 8 shows a section from a first or second detector of the detector arrangement viewed from the side.

The slots or channels which form the less sensitive areas 10, 12 can in accordance with the exemplary embodiment shown in FIG. 8 be filled with a material 27 of low absorption capability, in order to passivate the surfaces of the sensitive areas 9, 11 and/or increase the mechanical stability of the sensor.

Figure 9:
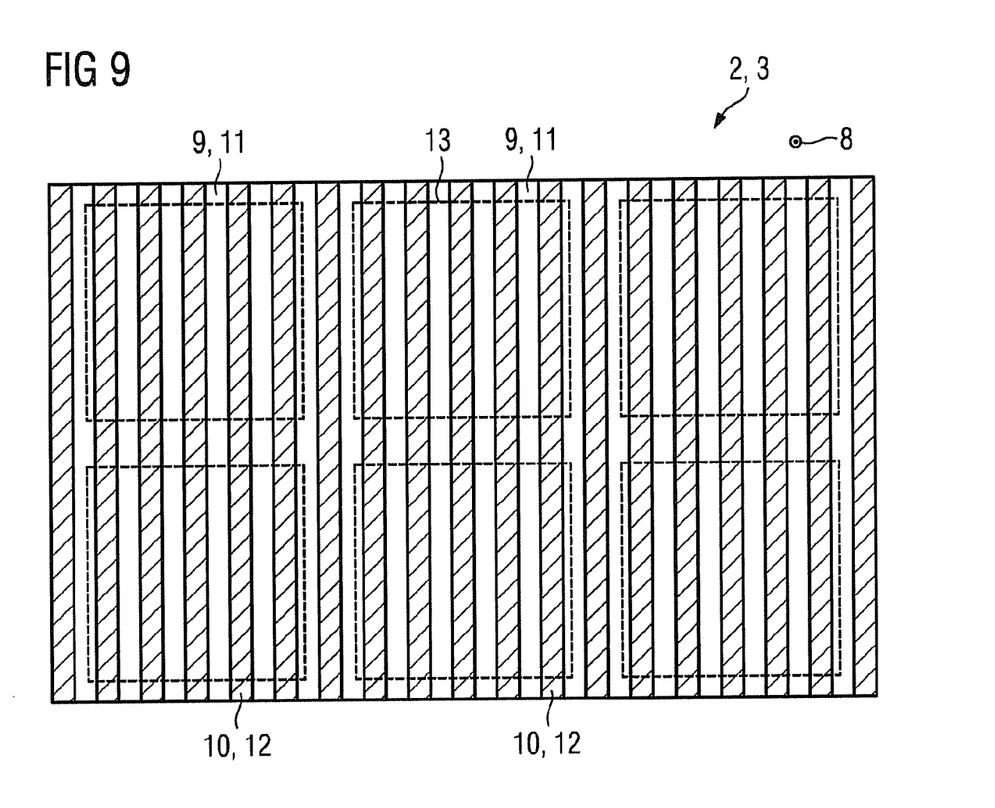
FIG. 9 shows a view from above of a first or second transducer layer with the pixel structure depicted as dashed lines.

FIG. 9 shows a view from above of one of the two transducer layers 2, 3 looking in the radiation direction 8 with the structure of the pixels 13 able to be seen in the form of dashed lines. A pixel 13 accordingly covers a number of sensitive and less sensitive strips 9, 10, 11, 12.

Figure 10:
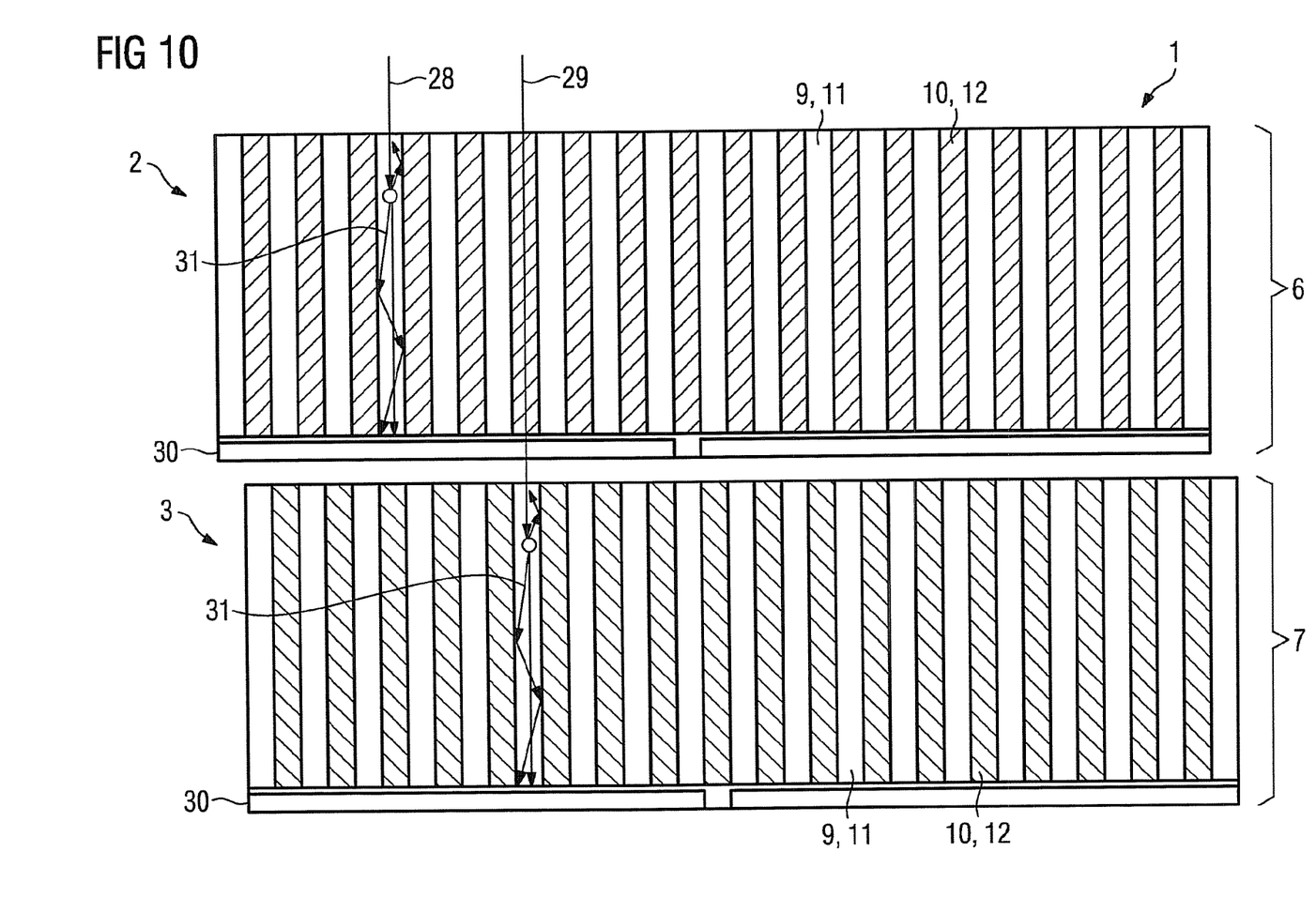
FIG. 10 shows a side view of a section of a third detector arrangement to illustrate the principle of interaction between X-ray radiation and the transducer layers.

FIG. 10 shows the principle of interaction of X-rays 28, 29 with a detector arrangement 1 in a view from the side, in which the detectors 6, 7 each comprise a transducer layer 2 3 in the form of a scintillator and an array of photodiodes 30. X-rays 28, which strike the sensitive strips 9 of the first transducer layer 2 are converted into light pulses 31 and are converted by the photo diode 30 coupled to the scintillator into electrical signals. X-rays 29 which strike the less sensitive strips 10 of the first transducer layer 2, pass through the first detector 6 and are subsequently converted in the sensitive strips 11 of the second transducer layer 3 into light pulses 31 and are converted by the photo diode 30 coupled to the scintillator into electrical signals.

At least one embodiment of the invention can be summarized as follows:

At least one embodiment of the invention relates to a detector arrangement 1 for performing phase-contrast measurements, comprising at least two transducer layers 2, 3 arranged behind one another, with at least the first transducer layer 2 arranged in the radiation direction 8 having in each case alternate sensitive areas 9 with a high absorptance for the conversion of incident ray quantas into signals and less sensitive areas 10 with a lower absorptance by comparison thereto. Phase-contrast images can be generated in this way with the same image quality compared to a grating-based measurement of a generated interference pattern with a lower X-ray dose within a shorter recording time. In addition a rapidly detected sequence of signals makes possible a correction of movement artifacts in the reconstructed image and/or a recognition and correction of changes in the sampling geometry.

At least one embodiment of the invention also relates to a corresponding X-ray tomography device 15 and to a method for performing phase-contrast measurements.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A detector arrangement for performing phase-contrast measurements, comprising
   at least two transducer layers formed of transducer material and arranged behind one another, at least a first of the at least two transducer layers arranged in a radiation direction including alternate sensitive areas, the alternate sensitive areas including sensitive areas with a relatively high absorption for the conversion of incident ray quantas into signals and less sensitive areas with a relatively lower absorption.

2. The detector arrangement as claimed in claim 1, wherein a second of the at least two transducer layers includes sensitive areas with a relatively high absorption for the conversion of incident ray quantas into signals and less sensitive areas with a relatively lower absorption, with one of the less sensitive areas of the second transducer layer following on in the radiation direction behind one of the sensitive areas of the first transducer layer, in each case, and wherein correspondingly one of the sensitive areas of the second transducer layer following on, in each case, behind one of the less sensitive areas of the first transducer layer.

3. The detector arrangement as claimed in claim 1, wherein the absorption of the less sensitive areas is reduced at least by a factor of 0.5 by comparison with the absorption of the sensitive areas.

4. The detector arrangement as claimed in claim 1, wherein at least one of the sensitive areas and one of the less sensitive areas include a width within a range of 0.5 µm to 20 µm.

5. The detector arrangement as claimed in claim 1, wherein the sensitive areas and the less sensitive areas are each embodied in a form of strips.

6. The detector arrangement as claimed in claim 1, wherein the at least two transducer layers are structured into pixels corresponding to one another for locally-resolved conversion of the incident ray quantas.

7. The detector arrangement as claimed in claim 6, wherein each pixel covers a number of sensitive areas and a number of less sensitive areas.

8. The detector arrangement as claimed in claim 1, wherein read-out electronics are arranged behind each of the at least two transducer layers in each case, which make electrical contact with a respective one of the first and second transducer layers.

9. The detector arrangement as claimed in claim 8, wherein the read-out electronics include a signal storage assigned to each pixel which is configured to buffer a sequence of detected electrical signals.

10. The detector arrangement as claimed in claim 1, wherein the at least two transducer layers are directly-converting and the semiconductor material is doped, the less sensitive areas being formed by slots or channels generated by one of photolithographic methods, etching methods or lasers.

11. The detector arrangement as claimed in claim 1, wherein the at least two transducer layers are indirectly-converting and include a scintillator in which the less sensitive areas are formed by slots or channels generated by one of photolithographic methods, etching methods or lasers.

12. An X-ray tomography device for performing phase contrast measurements, comprising:
an X-ray source including a coherence device configured to generate quasi-coherent X-rays;
a diffraction grating, arranged in a radiation direction behind an area under examination and configured to generate an interference pattern; and
a detector arrangement as claimed in claim 1, at least one of the detector arrangement, the diffraction grating and the coherence device being assigned an adjustment device with which the relative locations of at least two of the detector arrangement, the diffraction grating and the coherence device modified continuously or discretely modifiable in a direction perpendicular to the radiation direction.

13. The X-ray tomography device as claimed in claim 12, wherein the coherence device is a source grating.

14. The X-ray tomography device as claimed in claim 12, wherein the coherence device is electron optics for generating a plurality of focuses.

15. A method for performing phase-contrast measurements with an X-ray tomography device as claimed in claim 12, the method comprising:
reading out, at each sampling position for different relative locations perpendicular to the radiation direction between at least two of the coherence device, diffraction grating and detector arrangement, electrical signals for the pixels of the at least two transducer layers; and
computing the read out electrical signals into a phase-contrast image.

16. The method as claimed in claim 15, wherein, for the different relative locations of the at least two of the coherence device, diffraction grating and detector arrangement, a sequence of electrical signals for the pixels of the at least two transducer layers is detected and computed for at least one of a movement correction of the phase-contrast image and used for detection and correction of a changed sampling geometry.

17. The detector arrangement as claimed in claim 2, wherein the absorption of the less sensitive areas is reduced at least by a factor of 0.5 by comparison with the absorption of the sensitive areas.

18. The detector arrangement as claimed in claim 2, wherein at least one of the sensitive areas and the less sensitive areas include a width within a range of 0.5 µm to 20 µm.

19. The detector arrangement as claimed in claim 7, wherein the number of sensitive areas and less sensitive areas ranges from 10 to several hundreds.

20. An X-ray tomography device for performing phase contrast measurements, comprising:
an X-ray source including a coherence device configured to generate quasi-coherent X-rays;
a diffraction grating, arranged in a radiation direction behind an area under examination and configured to generate an interference pattern; and
a detector arrangement as claimed in claim 2, at least one of the detector arrangement, the diffraction grating and the coherence device being assigned an adjustment device with which relative locations of at least two of the detector arrangement, the diffraction grating and the coherence device continuously or discretely modifiable in a direction perpendicular to the radiation direction.

21. The X-ray tomography device as claimed in claim 20, wherein the coherence device is a source grating.

22. The X-ray tomography device as claimed in claim 20, wherein the coherence device is electron optics for generating a plurality of focuses.

* * * * *